United States Patent [19]

Wolfbeis et al.

[11] Patent Number: 4,965,087
[45] Date of Patent: Oct. 23, 1990

[54] METHOD OF MAKING A SENSOR ELEMENT FOR FLUORESCENCE-OPTICAL MEASUREMENTS

[75] Inventors: Otto Wolfbeis; Herbert Kroneis; Helmut Offenbacher, all of Graz, Austria

[73] Assignee: AVL AG, Schaffhausen, Switzerland

[21] Appl. No.: 172,959

[22] Filed: Mar. 23, 1988

Related U.S. Application Data

[60] Division of Ser. No. 876,667, Jun. 20, 1986, abandoned, which is a continuation of Ser. No. 558,342, Dec. 5, 1983, abandoned.

[30] Foreign Application Priority Data

Dec. 7, 1982 [AT] Austria ................. 4459/82
Nov. 17, 1983 [AT] Austria ................. 4047/83

[51] Int. Cl.$^5$ ............. G01N 21/64; G01N 31/22; B05D 1/36
[52] U.S. Cl. .................... 427/2; 422/57; 427/157; 427/203; 427/204; 436/163; 436/172
[58] Field of Search ............. 422/55, 56, 57; 436/163, 169, 172; 435/805; 427/2, 157, 203, 204

[56] References Cited

U.S. PATENT DOCUMENTS

| | | | |
|---|---|---|---|
| 2,986,453 | 5/1961 | Collins | 422/56 |
| 3,298,789 | 1/1967 | Mast | 422/56 |
| 3,418,083 | 12/1968 | Rey et al. | 436/169 X |
| 3,904,373 | 9/1975 | Harper | 436/169 X |
| 3,933,771 | 1/1976 | Eastman et al. | 524/569 X |
| 3,993,451 | 11/1976 | Verbeck | 422/57 |
| 4,003,707 | 1/1977 | Lubbers et al. | 436/178 X |
| 4,021,364 | 5/1977 | Speiser et al. | 424/33 X |
| 4,090,849 | 5/1978 | Healy et al. | 422/55 |
| 4,153,668 | 5/1979 | Hill et al. | 422/57 X |
| 4,160,666 | 7/1979 | McCabe et al. | 430/81 |
| 4,194,063 | 3/1980 | Frank et al. | 435/12 |
| 4,200,110 | 4/1980 | Peterson et al. | 436/163 X |
| 4,328,182 | 5/1982 | Blake | 422/56 |
| 4,568,518 | 2/1986 | Wolfbeis et al. | 422/56 |

FOREIGN PATENT DOCUMENTS 2360384 6/1974 Fed. Rep. of Germany.
2851138 6/1979 Fed. Rep. of Germany.

Primary Examiner—Mary Lynn Theisen
Attorney, Agent, or Firm—Watson, Cole, Grindle & Watson

[57] ABSTRACT

A sensor element useful in making fluorescence-optical measurements includes a substrate having a carrier surface, particles having a large specific surface are which are glued, melted or sintered onto the carrier surface so as to provide small elevations of a regular distribution on the carrier surface, and an indicator substance immobilized on the particles. Additional substances can be applied to the particles to reduce undesirable influences of properties of the sample on the indicator substance.

1 Claim, No Drawings

METHOD OF MAKING A SENSOR ELEMENT FOR FLUORESCENCE-OPTICAL MEASUREMENTS

This application is a division of application Ser. No. 876,667, filed June 20, 1986, now abandoned, which is a continuation of Ser. No. 558,342, filed Dec. 5, 1983, now abandoned.

BACKGROUND OF THE INVENTION

This invention relates to a sensor element for fluorescence-optical measurements, comprising a small carrier plate of preferably colourless, transparent or at least translucent appearance, which is provided with an immobilized fluorescent indicator substance on one side, and to a method of producing such a sensor element.

DESCRIPTION OF THE PRIOR ART

For the measurement of pH-values glass electrodes according to the potentiometric principle are widely used. For example, such sensors are employed for pH-analysis of biological fluids, e.g., for blood gas analysis. The main disadvantage of this method is that the entire system of measurement essentially consists of two parts, i.e., a measuring electrode and a reference electrode. In particular, measuring problems arise because the required reference electrode is subject to failure.

For this reason it has been attempted to measure pH-values by means of optical methods using so-called pH-indicators. Such methods are based on the utilization of a pH-dependent interaction of certain materials with light.

pH-indicators usually are molecules which can absorb light of a certain wavelength, the degree of this absorption depending on the pH-value. pH-measurements based on this absorption principle may be performed in two ways:

After adding pH-indicators to the sample material, the light absorption of the sample medium and the indicator is measured with suitable equipment (cuvette, photometer). The disadvantages of this method are high indicator consumption and expense of time, as well as optical influences exerted by the sample material.

The other alternative is described in German laid-open print No. 28 51 138, for instance, disclosing a fibre-optical pH-probe for implantation in tissues for physiological studies. This probe consists of an ion-permeable membrane in the shape of a hollow oblong cylinder, and two optical fibres arranged therein parallel to each other. The hollow membrane, whose pores should be permeable to hydrogen ions, is filled with a dyeing medium of pH-indicator properties. One of the two optical fibres is connected to a light source on its one end, whereas the other optical fibre is connected to the light detector. In this way the indicators are separated from the sample material such that two chambers are formed, one for the sample material and one for the indicator material. An exchange of protons between indicator and sample material chambers will permit the pH-value of the sample material to be determined by measuring light absorption in the indicator chamber.

As pH-indicators with the above properties, fluorescent molecules may be used to advantage. In this case a certain percentage of the light absorbed is given off as fluorescent light by the indicator molecule. If the light absorption of a fluorescent molecule actually is pH-dependent, this dependency is transmitted to the intensity of the fluorescent light. Thus, pH-values can be determined by measuring the intensity of the fluorescent light of fluorescent pH-indicators. Such indicators are listed in "Practical Fluorescence" (Guilbault, 1973), for example, in the chapter on "Fluorescent Indicators".

Among the advantages resulting from the use of fluorescent indicators are high sensitivity, spectral distinction between excitation and emission light, and a great variety of possible locations of light source and light receiver.

These benefits will allow measuring devices to be configured such that planar layers of indicator material will interact with the sample material on one side, whereas the other side of such layers is provided with lighting and light-measuring devices.

When manufacturing such planar layers of indicator material, it must be borne in mind that the indicator molecules should not be washed out by the sample material. They should, however, be permitted to interact with the protons of the solvent. In addition, the planar indicator layer should be mechanically stable and the concentration of the indicator substance should be sufficiently high.

pH-indicators are immobilized in hydrophilic polymer membranes by covalent bonding of the indicator and the membrane material. For this purpose either the indicator or the polymer membrane—or both—must be provided in activated form.

Activation is usually achieved by introducing reactive groups, for example, amino groups. In this way indicator substances such as $\beta$-methylumbelliferone or fluorescein derivatives have been successfully bonded to cellulose.

Indicators may also be immobilized by encapsulation in suitable materials, e.g., as described in German laid-open print No. 23 60 384. Such "nanocapsules" are filled with aqueous indicator solution; the wall of the capsule is permeable to protons but impermeable to the indicator substance.

For the manufacture of pH-sensors these capsules in turn will have to be immobilized in planar array.

Mechanical instability, low indicator loading densities and poor response times are but some of the drawbacks of these known and described types of pH-sensors.

Another possibility of immobilizing pH-indicators is by bonding the indicators to the surface of a transparent carrier which is inert and mechanically stable.

The obvious method presenting itself is immobilization of the pH-indicator on a chemically reactive material whose mechanical properties are less suited, e.g., cellulose, which is then placed on a stable and transparent carrier, such as glass or polyacrylic ester.

This method of immobilizing fluorescent indicators on cellulose or glass is known. It uses cellulose or glass to which a free amino group has been attached in one or several preceding steps of reaction. The reactive groups of an indicator, e.g., fluorescein isothiocyanate, will then react on this amino group.

All known methods of immobilization on glass surfaces suffer from the disadvantage that the surface will accept only a relatively small amount of immobilized indicator bonded in a single layer.

SUMMARY OF THE INVENTION

It is the object of the present invention to produce a simple sensor element comprising an immobilized indicator in a single layer which has been bonded to a substrate or carrier of sufficient mechanical stability in such a way that it does not wash out, and to provide for the concentration of this indicator to be high enough so as to obtain a high signal-to-noise ratio during measurement.

According to the invention this is achieved by providing that side of the carrier holding the immobilized indicator substance with small elevations of a uniform distribution pattern, i.e., by glueing, sintering or melting particles having a large specific surface onto the noted side of the carrier. In this way a large reaction area for surface immobilization of the indicator substance will be obtained.

A preferred method of producing such a sensor element according to the invention is characterized by, firstly, bonding particles of a high specific surface area to a carrier surface by glueing, sintering or melting them on, and, subsequently, by immobilizing an indicator, possibly by covalent bonding, on the accessible surface of the bonded particles. This is to say that the surface of the carrier side of the substrate is modified according to the invention before the indicator is immobilized on it, which will prevent the process of glueing, melting or sintering from affecting the indicator molecules or their immobilization.

In another variant of the invention the first step may consist of applying an indicator substance, possibly by covalent bonding, to the surface of particles with a high specific surface area, and then bonding these indicator-loaded particles to a carrier surface by glueing, melting or sintering.

In a preferred form of the invention the accessible surfaces of the particles which have already been bonded to the carrier surface are, prior to immobilization of the indicator, chemically activated in a known manner with acids or acid mixtures, e.g., a mixture of concentrated sulphuric and nitric acids, so as to enhance the subsequent formation of bonds with the indicator substance.

A typical sensor element according to the invention comprises a small carrier plate of glass or plastic. For increasing the surface area, some pelletized material (particles, beads) may be applied on this plate to establish a firm bond, and the pellets may be provided with the immobilized indicator before they are bonded to the carrier. In this case the pellets, which may be made of glass, plexiglass, synthetic resins, etc., are applied with the use of an adhesive, for instance a polyurethane coating featuring toughness, good adhesion and low swelling despite good wetting properties.

Other ways of increasing the surface area would include coarse and fine grinding, sandblasting, etching, scratching or moulding in a surface pattern during manufacture.

It has been found that, in sensor elements as described by the present invention, wherein the indicator molecules proper are located at the interface between the carrier and sample medium, the properties of the sample medium are not entirely negligible, above all if a high accuracy of measurement is required.

For instance, in oxygen sensor elements whose $pO_2$ sensitivity is based on the phenomenon of fluorescence extinction by molecular oxygen, it has been observed that signals obtained in gas analysis are influenced by the degree of humidity of the gases to be measured, although it is known that water will not extinguish fluorescence. Besides, deviating values have been measured, e.g., in the course of fluorescence-optical pH-measurements with sensor elements as described, on account of differences in the ionic strength of the sample measured.

In order to avoid the above drawbacks which may be experienced under certain circumstances and to eliminate or at least reduce undesirable influences of the sample medium which may affect measurement accuracy, another development of the invention may provide that at least one further substance is applied to the surface carrying the immobilized indicator, such that the microenvironment of the indicator substance is protected, at least partially, from the influences of the sample. Microenvironment in this context denotes that portion of the space surrounding the indicator molecules within which the sample as a whole will be able to influence the interaction between indicator and test material proper, or rather, within which the indicator will be susceptible to influences exerted by the sample as a whole.

This variant of the invention is therefore based on the finding that the changes in the fluorescence signal, which should essentially be proportional to the concentration of the sample material to be measured, are additionally influenced by an interaction between the indicator and the sample to be measured. Such interactions in turn are influenced by the properties of the microenvironment of the indicator, which are physical and/or chemical in nature, and which are modified in turn by the presence of the sample, of course. This is of great importance, especially in sensor elements of the above type, since in such elements indicators which have been superficially attached to the enlarged surface area of the carrier will project into the sample medium, causing the physical and chemical properties of the indicator microenvironment, such as solubility of substances, mass transport phenomena, ionic environment and others, to be co-determined by the respective properties of the sample.

In a further development of the invention the additional substance carries hydrophobic and/or ionic groups which are attached to the carrier surface through covalent bonds. When measuring pH-values, for example, the dependence of the measured value on the ionic strength of the test sample may be drastically reduced. In an enhanced variant, the ionic groups may consist of dipolar ions, e.g., amino acids, in which case the charges of the groups bonded to the carrier surface will compensate each other. Thus the ionic character of the indicator microenvironment is at least partially determined, and the influence on the indicator molecules, which is exerted by the ionic strength of the sample, is therewith reduced. In this context it would also be possible to use substances of a high ionic strength as ionic groups, which do not affect the measurement itself, e.g., pH-measurement; this would also counteract the influence of the ionic strength of the sample and would reduce it, depending on the given ionic strength of the additional substance.

According to another proposal of the invention a second protective substance (in addition to the first protective substance noted above) is chemically bonded to the carrier, the second protective substance having dialkyl or trialkyl silyl groups as hydrophobic residues. By thus populating the carrier surface with hydrophobic molecules, a hydrophilic sample is at least partly separated from the carrier surface and thus from the indicator molecules bonded to this surface. In this manner siliceous substrates may be rendered hydrophobic by modification with dichlorodialkyl silane or chlorotrialkyl silane, upon which the substrate will carry the above silyl groups on its surface.

In yet another development of the invention the additional substance preferably consists of a polymer coating covering the carrier side holding the indicator. This will permit the sensor element to be sealed tightly, which will keep off selected undesirable sample components from the microenvironment of the indicator molecules, and will thus reduce the undesired influence of the sample on the result of the measurement proper.

In this respect the invention may be enhanced by the use of hydrophilic polymers, such as cellulose derivatives, as additional substance, which will permit the coating of sensor elements for pH-measurement, for instance, in order to reduce the influences of the ionic strength of the sample.

In another development of the invention hydrophobic polymers such as silicone rubbers are proposed for use as additional substance, which will permit the coating of sensor elements, for instance for determination of oxygen partial pressures.

DESCRIPTION OF VARIOUS EMBODIMENTS

Other features and benefits of the present invention will now be decribed by way of practical examples.

In order to produce sensor elements of satisfactory mechanical strength and a particularly large surface area for total take-up of the immobilized indicator, the indicator is directly immobilized on a chemically activated binder, e.g., silica gel, which is then bonded to a rigid transparent carrier such that the indicator is first attached to the surface-active material (silica gel) with its large specific surface area. The latter will then be applied by suitable techniques (e.g. with the use of an adhesive) to a rigid transparent substrate (glass, plexiglass). Out of numerous known adhesives a polyurethane coating (No. PU 428, VIANOVA) has proved best because of its toughness, good adhesion to plexiglass and the low swell in spite of good wetting properties. With the use of this coating indicator pellets will firmly adhere to plexiglass or glass.

Furthermore, it will also be possible to attach some chemically suitable material, e.g., silica gel or glass pellets, to a rigid carrier by means of an adhesive agent or heat-treatment (sintering), following which the indicator is chemically immobilized on the surface-increasing substance bonded to the carrier.

By melting this substance onto the carrier a rough and reactive surface of good stability will be obtained instead of the smooth glass surface with its low reactivity. On this rough surface the indicator may be immobilized by various chemical processes. The sensor elements obtained in this way are characterized by high loading densities and good signal response times.

The surface area of the carrier could also be increased by etching, coarse or fine grinding, scratching or moulding-in of a suitable structure during manufacture of the carrier, and the small elevations and depressions resulting from such processes could be of regular or irregular shape.

Besides, the composition of the substances to be melted or glued on may vary greatly. Glass may be used just as well as synthetic resins, silica gel, etc.; the same applies to the carrier material itself.

According to the present invention, the following steps should be taken for production of a sensor element employing silica gel. Bonding of the immobilized indicator to a carrier of polymethyl methacrylate is achieved by means of a polyurethane coating curing under the influence of atmospheric moisture, as described below:

The polyurethane coating PU 428, 42% in xylene (VIANOVA KUNSTHARZ) is applied to the carrier plate by means of an edge-cut glass slide. The immobilized indicator is spread on the wet film of synthetic resin such that a uniform distribution is achieved, leading to a monogranular layer of silica gel. The plate is oven-cured for 30 minutes at 80° C. After a drying period of 24 hours at room temperature, the sensor element should be activated by saponification of the acetoxy and sulphonyl chloride groups, i.e., by soaking the plate for 2-3 hours in a pH 8 phosphate buffer 1/15 M. After a short rinse in water the sensor element will be ready for use.

Immobilization of an indicator on silica gel is achieved as follows:

As a carrier substance silica gel is used (e.g. Merckosorb Si 60), which is activated for immobilization in the following manner: Prepare an acid mixture of 1 part concentrated nitric acid and 1 part concentrated sulphuric acid, gently stir in silica gel with a glass rod and allow to stand for 4 hours. Remove the slurry with a glass filter and rinse the silica gel until rinsing water exhibits a pH-value of approximately 4.5; allow to dry over night at 100° C. Prepare a solution of 22.2 mg acetoxyprene-3,6,8-trisulphonyl chloride in 10 ml of absolute dioxane in a 100 ml flask and add 2 drops of pyridine.

Add slowly while stirring (dropwise addition over 10-15 minutes) a solution of 8.4 $\mu$l triethoxysilyl propylamine in 5 ml dioxane. Stir solution for approximately 5 minutes and add 0.4 grams of activated silica gel. In order to prevent silica gel from being crushed during stirring, the stirrer should be lifted such that stirring will take place only in the top layer of the clear supernatant solution. Slowly add to this formulation 5 ml dioxane containing 0.05 ml water as a catalyst, stirring gently at reflux. After a reflux of 150 minutes, immobilization is complete. Filter off the immobilized substance by suction, elute with dioxane for 1 hour, rinse in acetone until no trace of yellow is left and oven-dry at 60° C.

Another possibility of producing a sensor element is as follows: Cut a piece of glass (window-glass, microscope slide) to the desired size. Sprinkle a flat cake of talcum with talcum powder to a build of 1 mm approximately, and gently press the glass plate onto this layer. Sprinkle the plate with glass powder (CPG 10-170 Å, FLUKA, Switzerland) or silica gel (e.g. Merckosorb Si 60, MERCK, West Germany) to a thickness of 0.5-1.0 mm. After sintering for 40 minutes in a muffle furnace at 720°-800° C, remove the plate, allow it to cool, and blow off the excess powder. When CPG (controlled-page glass) is used, the particles thereof will become partially embedded in the surface of the glass plate (the glass plate will become softened at 720° to 800° C. whereas the particles of CPG will retain their integrity). The glass plate is activated for 2 hours at room temperature with a mixture of concentrated sulphuric and nitric acids, and rinse thoroughly (2 hours) with distilled water; vacuum-dry at 120° C. Immobilization is achieved as described for silica gel above, except that 200 ml of solvent should be used, and 20 of the newly prepared glass plates instead of 0.4 g silica gel should be added. The glass plates obtained in this manner will have a sintering zone of a yellow colour. After soaking in a phosphate buffer solution pH 8 for 48 hours, they will be ready for service.

Other examples of indicator immobilization include:

Immobilization of 1-acetylpyrene-3,6,8-trisulphonic acid trichloride to $\mu$-Bondapak-NH$_2$:

Suspend 100 mg Bondapak powder ($\mu$-Bondapak-NH$_2$, item No. 84155, WATERS) in 5 ml water. Add 0.5 ml of a solution of .15 mg solution of 4 mg 1-acetoxypyrene-3,6,8-trisulphonyl chloride in 10 ml dioxane. Filter off by suction after 5 minutes, and rinse twice with 5 ml of a 20 % sodium carbonate solution. After a final rinse in water, a powder of a pale yellow colour will be obtained.

Immobilization of fluorescein to $\mu$-Bondapak-NH$_2$ silicate pellets:

Add 0.5 ml of a solution of 1 mg fluorescein isothiocyanate in 10 ml water to a suspension of 100 ml $\mu$-Bondapak-NH$_2$ (WATERS) in 5 ml water. After 5 minutes filter off product by suction and rinse with water. The powder obtained will have a yellow colour.

The following examples will serve to illustrate the steps proposed by the present invention for reducing or eliminating the disturbing influences exerted by the sample.

(a) Surface modification of the carrier in pH sensor elements

Influences exerted by the sample medium are to be reduced by the partial removal of sample components from the microenvironment of the indicator.

The disturbance from the sample is caused by fluctuations of the ionic environment of the sample which will lead to fluctuations of the measured pH-values.

There are two possible remedies: Either the sample as such is kept away from part of the microenvironment of the indicators, or the species causing a disturbance, i.e., a component of the sample, is kept away, at least partly, from the microenvironment of the indicator.

In the former case, the surface carrying the indicator may be rendered hydrophobic, for example. In case of hydrophilic or charged surfaces a direct contact between carrier surface and the hydrophilic (aqueous) sample medium must be expected. By filling the carrier surface with hydrophobic molecules—the substances and methods of filling may be of a conventional type—the hydrophilic sample is, at least partly, separated from the carrier surface and thus from the indicator molecules adhering to it.

In this manner siliceous substrates may be rendered hydrophobic by modification with dichlorodialkylsilane or chlorotrialkylsilane (24 hours cooking to reflux). As a result, the carrier surface obtained in this way will carry dialkyl or trialkyl groups.

In the other case, i.e., if only part of the sample is kept away from the microenvironment of the indicators, an equally efficient method would be to attach ions to the carrier surface for the indicator, in addition to the indicator itself. The ionic character of the indicator microenvironment thus is partially determined, and any influence via the ionic strength of the sample will be reduced. This method will be most efficient if the charges of the ions attached to the carrier surface neutralize each other, i.e., if the surface exhibits approximately the same number of positive and negative charges, as for instance when dipolar ions (amino acids) are attached.

A combination of hydrophobing and ion attaching processes has also proved useful.

(b) Polymer coating of the carrier in pH sensor elements pH sensor elements (as described, for example, on pages 7–9) are coated with a solution of a hydrophilic polymer substance, e.g., a solution of cellulose acetate or cellulose nitrate in acetone. After evaporation of the solvent a hydrophilic polymer coating will remain on the sensor, which will largely determine the microenvironment of the indicators and will greatly reduce any influences due to the ionic strength of the sample, for instance.

(c) Polymer coating of the carrier in pO$_2$ sensor elements Production of pO$_2$ sensor elements:

The production of pO$_2$ sensor elements essentially follows that of pH sensor elements. Suitable indicators include polycyclic aromatic hydrocarbons with one or several carboxylic acid groups on one or several side-chains, e.g., pyrene butyric acid, decacyclene butyric acid, perylene dibutyric acid, benzo(ghi)perylene butyric acid, etc.

Coating of pO$_2$ sensor elements:

For the coating of oxygen sensor elements a hydrophobic, oxygen-permeable polymer substance is used, or rather a pre-mix of this material, which may be poured or brushed on or is at least mouldable. Suitable materials include commercial stocks which may be cured to form silicone rubbers, such as Elastosil E 41 (WACKER), Elastosil N 189 (WACKER), and most types of RTV-1, RTV-2 or HTV silicone rubbers.

For better dispersion the commercially available base stock may be diluted with solvents already present in the material (toluene, xylene). Preferably, silicone coatings should be used in combination with siliceous substrates, as the affinity of the materials will ensure particularly good adhesion of the coating.

Coatings are applied by pouring, brushing or moulding the polymerizable material or the polymer solution onto the surface of the sensor to which the indicator has already been bonded. After curing of the polymer and evaporation of the solvents the sensor element will be ready for use. The properties of the indicator will be determined by its microenvironment of oxygen-permeable hydrophobic polymer material.

Whereas surface modification by the addition of hydrophobic or ionic groups will only slightly affect the response times of the sensor, the influence of the sample cannot be totally eliminated. On the other hand, the coating method will permit well-defined conditions in the microenvironment of the indicators. Besides, this method will permit optical de-coupling between sensor and sample material in a simple manner, by the incorporation of inert pigments or dyes into the polymer coating. The disadvantage of prolonged response times may be counterbalanced by reduced film thicknesses.

I claim:

1. A method of providing a sensor element which is useful in making fluorescence-optical measurements of the pH value of a physiological sample having an ionic strength, the sensor element having a high mechanical stability and a reduced susceptibility to the influence of the ionic strength of such a physiological sample, said method comprising the steps of
    (1) providing a transparent carrier plate which is made of glass and has opposite surfaces,
    (2) distributing microporous glass particles on one of said opposite surfaces of said transparent carrier plate and heating to a temperature of about 720° to 800° C. to partially embed the microporous glass particles in a uniform distribution in said surface of said transparent carrier plate so as to leave projecting portions which extend outwardly from said one surface of said transparent carrier plate, the projecting portions of said microporous glass particles providing a microporous layer on said one surface of said transparent carrier plate, (3) contacting the projecting surfaces of said microporous glass particles with an acid selected from the group consisting of sulphuric and nitric acid to activate the projecting surfaces, (4) chemically bonding a fluorescent indicator substance to the activated projecting portions of said microporous glass particles so as to become immobilized with respect to said carrier plate, and (5) chemically bonding first and second protective substances to the projecting portions of said microporous glass particles so as to become immobilized with respect to said carrier plate, said first protective substance including ionic groups which reduce the influence of the ionic strength of a physiological sample on said fluorescent indicator substance and said second protective substance including hydrophobic groups which render exposed portions of said transparent carrier plate inert, each of said first and second protective substances preventing unwanted changes in fluorescence of said fluorescent indicator substance due to contact with a physiological sample.

* * * * *